(12) United States Patent
Bazzoni

(10) Patent No.: US 10,154,356 B2
(45) Date of Patent: Dec. 11, 2018

(54) PROCESS AND ARCHITECTURE FOR REMOTELY ADJUSTING A HEARING AID

(71) Applicant: DIGITAL TALES S.R.L., Milan (IT)

(72) Inventor: Giovanni Luigi Bazzoni, Milan (IT)

(73) Assignee: DIGITAL TALES S.R.L., Milan (IT)

( * ) Notice: Subject to any disclaimer, the term of this patent is extended or adjusted under 35 U.S.C. 154(b) by 0 days.

(21) Appl. No.: 15/570,556

(22) PCT Filed: Apr. 28, 2016

(86) PCT No.: PCT/IB2016/052406
§ 371 (c)(1),
(2) Date: Oct. 30, 2017

(87) PCT Pub. No.: WO2016/174603
PCT Pub. Date: Nov. 3, 2016

(65) Prior Publication Data
US 2018/0146310 A1 May 24, 2018

(30) Foreign Application Priority Data

Apr. 30, 2015 (IT) .......................... 102015000013659
Apr. 30, 2015 (IT) .......................... 102015000013678

(51) Int. Cl.
*H04R 25/00* (2006.01)
*G06F 19/00* (2018.01)
(Continued)

(52) U.S. Cl.
CPC ........... *H04R 25/558* (2013.01); *G06F 19/00* (2013.01); *G06F 19/3418* (2013.01);
(Continued)

(58) Field of Classification Search
CPC ...... H04R 25/00; H04R 25/55; H04R 25/558; H04R 2225/49; H04R 2460/01
(Continued)

(56) References Cited

U.S. PATENT DOCUMENTS

| 2011/0176697 A1* | 7/2011 | Apfel | H04R 25/305 |
| | | | 381/314 |
| 2011/0293123 A1* | 12/2011 | Neumeyer | H04R 25/50 |
| | | | 381/314 |

(Continued)

*Primary Examiner* — Suhan Ni

(57) ABSTRACT

Process for remotely adjusting a hearing aid, wherein telemetric data representative of the acoustic environment in which the hearing aid (10) is operating and/or of the behavior thereof in response to this environment is acquired from said hearing aid, said process comprising the following steps: —downloading said telemetric data from the hearing aid to a user-side multimedia device (200); —acquiring by means of the multimedia device (200) diagnostic data for the current operation of the hearing aid, which is saved in the said multimedia device (200); —forwarding to a server-side server (300) the saved diagnostic data; —forwarding the current telemetric data downloaded from the hearing aid from the multimedia device (200) to the server (300); —preparing current configuration data for operating parameters of the hearing aid on the server-side server; —processing on the server side a new configuration profile on the basis of the telemetric data and diagnostic data received; —sending the new configuration profile data to the multimedia device (200); —forwarding the new configuration data to the hearing aid (10), for a new configuration thereof.

33 Claims, 2 Drawing Sheets

Figure 1:
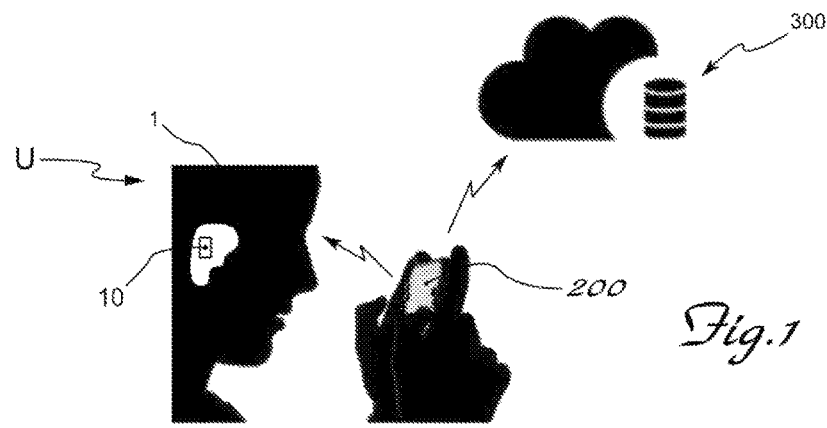

(51) Int. Cl.
*G16H 40/40* (2018.01)
*G16H 40/67* (2018.01)

(52) U.S. Cl.
CPC ............ *G16H 40/40* (2018.01); *G16H 40/67* (2018.01); *H04R 25/70* (2013.01); *H04R 25/554* (2013.01); *H04R 2225/39* (2013.01); *H04R 2225/41* (2013.01); *H04R 2225/55* (2013.01)

(58) Field of Classification Search
USPC .................... 381/312, 315, 317, 320, 331
See application file for complete search history.

(56) References Cited

U.S. PATENT DOCUMENTS

| | | | | |
|---|---|---|---|---|
| 2012/0183165 A1* | 7/2012 | Foo | ............. | H04R 25/50 381/314 |
| 2016/0173999 A1* | 6/2016 | Ungstrup | ............. | H04R 25/554 381/315 |
| 2016/0212552 A1* | 7/2016 | Schneider | ............. | H04R 25/558 |

* cited by examiner

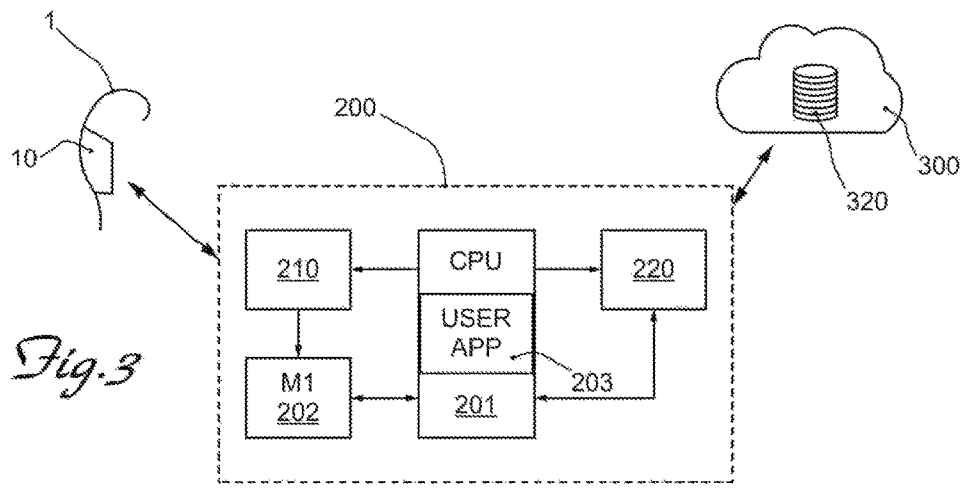
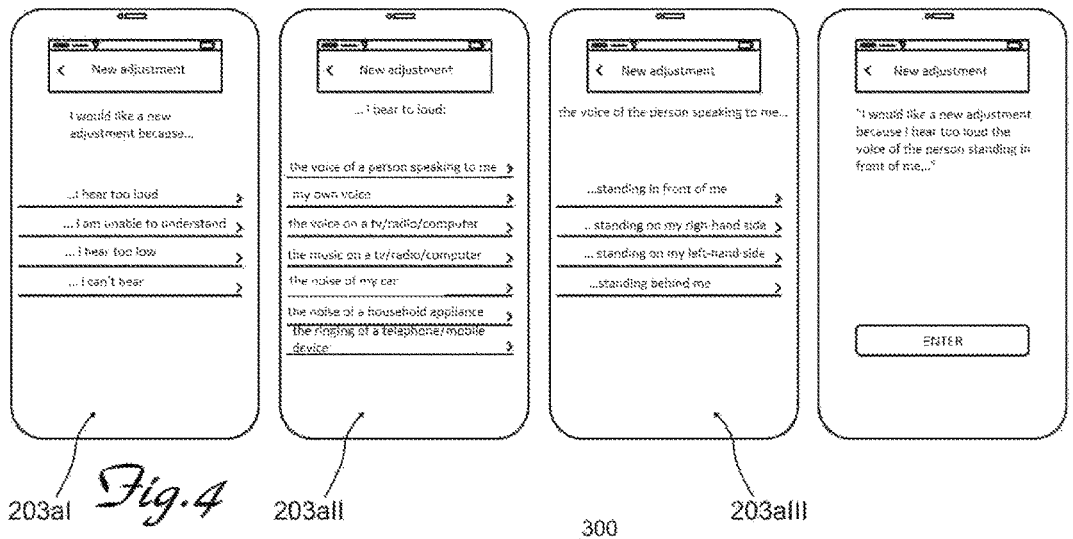
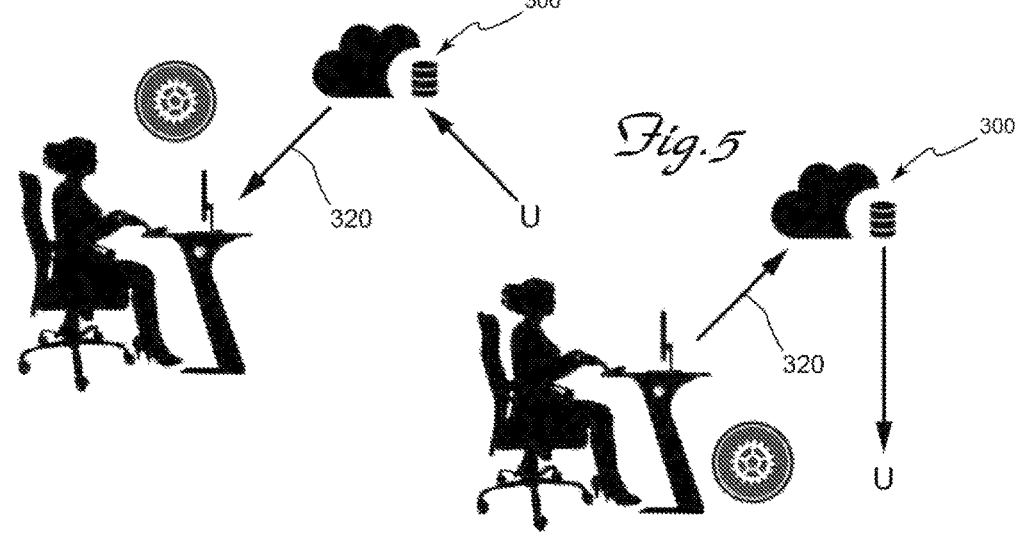

PROCESS AND ARCHITECTURE FOR REMOTELY ADJUSTING A HEARING AID

The present invention relates to a process for remotely adjusting a hearing aid and to a hearing aid architecture for implementing such a process.

It is known, in the technical sector relating to hearing aids, such as auxiliary hearing apparatus for users with hearing difficulties, that the said apparatus require frequent recalibration or adjustment in order to better adapt the different operating parameters to specific situations, needs and/or hearing defects of the user.

It is also known that, according to the current state of the art, any adjustment or recalibration of the hearing apparatus is performed by qualified hearing aid specialists who operate in specialized laboratories where the user of a hearing aid must go whenever the device has a problem or is not working properly.

At the laboratories, the user explains the problem(s) encountered and his/her own particular needs to the hearing aid specialist who, on the basis of this information, calculates new values for the configuration parameters of the hearing apparatus, setting them in the apparatus.

Such procedures, while fulfilling their function, have a number of problems:
- firstly the fact that the user has to go a specialized centre whenever there is a problem with the apparatus or if it is not working properly, results in a great loss of time as well as organizational difficulties for example due to the advanced age of the users or the need to abandon the activities being performed because they are unable to hear correctly;
- in addition the apparatus maintenance service is not available outside of the working hours of the laboratories and it is not always possible to use the same operator or the same laboratory (for example if the problem arises while travelling);
- the user is therefore required to explain the problems and related conditions to each different hearing aid specialist or laboratory;
- in addition to the above the user is required to return to the specialized laboratory for further more finely tuned adjustments, should the procedure not have produced satisfactory results.

WO 2015/024585 A1 describes a method according to the preamble of claim 1, in which a hearing aid is adapted to self-adjust its current operating parameters in response to telemetric data acquired from the hearing aid itself and indicating a problematic acoustic environment and on the basis of a statistical analysis of said telemetric data; and in which a multimedia device possessed by the user comprises an auxiliary classifier able to assist the hearing aid during its attempted self-adjustment operation with further information relating to the acoustic environment identified by positional and/or behavioural data relating to the user and acquired by the device; and in which the multimedia device also allows the user to indicate to the hearing aid that a self-adjustment operation performed is not effective.

Once the self-adjustment has been performed, the new adjustment data is sent to an external server, together with an indication of the degree of satisfaction of the user expressed in the form of a numerical scale, so as to create a database containing statistical and adjustment information for several users, aimed at improving future general or specific adjustments for certain acoustic environments, based on a statistical analysis of said data.

If the self-adjustment (performed by the hearing aid on its own or with the aid of the external classifier) is not effective, the multimedia device asks the user to request a new adjustment from an external server and, upon acceptance by the user, sends to the external server:
- a request for new adjustment;
- a current configuration of the operating parameters;
- a historical record of relevant data.

The server provides a new adjustment automatically or with the aid of a hearing aid specialist; no detail is provided in WO'585 as to the nature of the data sent or as to how the adjustment may be performed by the server.

All the adjustments described in the document are based only on statistical analyses of data representative of the environment in which the hearing aid is operating and/or on the operating behaviour thereof in response to said environment, said data being comparable with telemetric data as mentioned in the preamble of Claim 1.

The technical problem which is posed, therefore, is to provide an improved process and a hearing aid architecture for the adjustment/recalibration of a hearing aid according to the needs or problems encountered by a user, which provide a solution to the problems of the prior art.

In connection with this technical problem it is also required that the process and the architecture should allow assistance as rapidly as possible and not require the user to have to visit specialized laboratories.

In addition, it is desirable that such a process and architecture should be easy and inexpensive for any user to employ using normal standard connection means.

These results are obtained according to the present invention by a process for remote adjustment of a hearing aid adapted for remote adjustment and by a hearing aid architecture according to the herein described subject matter.

An example of a hearing aid particularly suitable for remote adjustment may comprise:
- a processing and control processor (10a),
- at least one memory (16), for saving a set of data forming a configuration profile, on the basis of which the processor (10a) adjusts various parameters for adjusting operation of the hearing aid;
- microphone transducer means (11a;11b);
- a block (12) for managing the microphone recording configuration, by processing audio signals emitted by the microphone transducer means (11a;11b) and outputting an audio signal (s12) which emulates an audio signal acquired with a microphone detection configuration defined on the basis of the current configuration profile;
- a Speech/Noise manager (13) for preliminary handling of the audio signal emitted by the microphone management block (12), the manager (13) being designed to perform a preliminary analysis and pre-processing in terms of signal/noise ratio of the signal (s12) emitted by the microphone management block (12);
- a block (14) for distributing the signal (s13) emitted by the manager (13) over several frequency channels, so as to output a plurality (n) of signals (s141,s142, . . . ,s14n) distributed over corresponding (n) frequency channels (Ch1, . . . ,Chn);
- a block (15) for independently processing each channel (Ch1, . . . , Chn), comprising at least one element (151,152, . . . ,15n) for adjusting the gains of each channel;

wherein downstream of the independent channel processor (15) the processed signals (s15i) of all the channels are recombined (15b) and transferred to an output (s15);

at least one loudspeaker (19) for transmission, in the auditory canal of a user (U), of the audio signal output by the hearing aid (10);

wireless communication means (18) for connection to a multimedia device (200).

According to an aspect of the present invention, the hearing aid (10) is designed to acquire telemetric data indicating characteristics of the acoustic environment in which the hearing aid is operating and/or indicating an operating behaviour of the hearing aid (10) in response to said environment, so as to allow remote adjustment of the hearing aid.

The process comprises the steps of:

acquiring from the hearing aid (10) telemetric data representative of the acoustic environment in which the hearing aid is operating and of the operating behaviour of the hearing aid (10) in response to this environment, downloading said telemetric data from the hearing aid to a user-side multimedia device (200) of a remote adjustment system;

acquiring by means of the multimedia device (200) diagnostic data for the current operation of the hearing aid, which is entered by the user and saved in the said multimedia device (200);

forwarding the diagnostic data saved in the multimedia device (200) to a server-side server (300) of the remote adjustment system;

forwarding the telemetric data downloaded from the hearing aid from the multimedia device (200) to the server (300);

providing current configuration data for operating parameters of the hearing aid to the server-side server;

wherein:

the telemetric data acquired and forwarded to the server (300) comprises current telemetric data acquired from the hearing aid (10) following a request/command sent from the multimedia device (200) to the hearing aid (10) and acquired and/or saved as an average of respective instantaneous recordings within a predefined time interval;

during acquisition of the said diagnostic data the user is requested to enter information relating to one or more hearing problems and/or defects relating to the current operation of the hearing aid (10) in the acoustic environment in which the hearing aid is operating with the current configuration of the operating parameters, and said information is saved in at least a first set (I) of said diagnostic data and forwarded from the multimedia device (200) to the server (300);

and said information entered by the user is associated in the adjustment system with objective diagnostic information relating to the current operation of the hearing aid in the acoustic environment in which it is operating;

the process comprises a step of processing at the server side new configuration data for operating parameters of the hearing aid, adjusting at least one parameter of the current configuration on the basis of an analysis of the objective diagnostic information associated with the current diagnostic data received correlated with an analysis of the current telemetric data received;

wherein the process comprises the further steps of:

sending the new configuration data of the hearing aid (10) to the multimedia device (200);

forwarding the new configuration data from the multimedia device (200) to the hearing aid (10), for a new configuration thereof.

Preferred aspects of the invention are indicated in the dependent claims, which are cited here in full.

Figure 2:
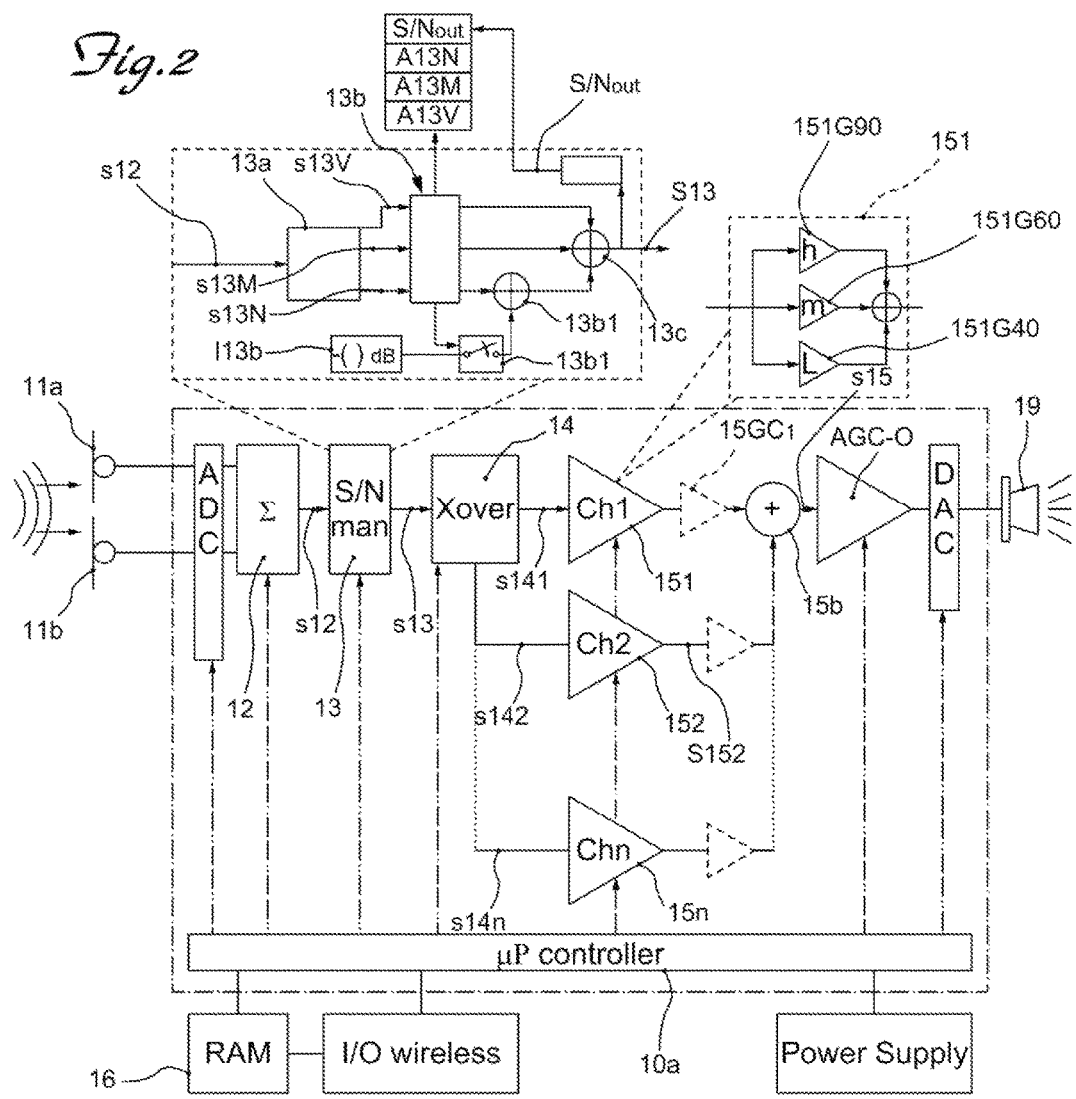

Further details may be obtained from the following description of non-limiting examples of embodiment of the subject of the present invention, provided with reference to the accompanying drawings, in which:

FIG. 1: is a schematic view of a user with a hearing aid and a multimedia device connected to a server of an adjusting system of a hearing aid architecture which implements a process according to the invention;

FIG. 2: is a logic diagram of a multimedia device of the system according to FIG. 1;

FIG. 3: is a circuit logic diagram of an example of embodiment of a preferred hearing aid for remote adjustment using a process according to the invention;

FIG. 4: is an illustration of an example of embodiment of a user interface for a diagnostic tool of a user application for a multimedia device of a process according to the invention;

FIG. 5: shows schematic views of an example of implementation by the server side of some steps of a process according to the invention.

Assuming for the sake of convenience of the description and without a limiting meaning, an uplink direction corresponding to a communication from the user side to the server side and a downlink direction for communication from the server side to the user side of a system which implements a method according to the invention, FIG. 1 shows a user U wearing a hearing apparatus 10. The user U shown in FIG. 1 also has a multimedia telecommunication device 200 comprising a user application 203; the device 200 forms part of a system for adjusting the hearing aid, which also comprises a server side 300.

With reference to FIG. 3, in a preferred process and architecture according to the invention, the multimedia device 200 comprises at least:

means (210) for communication with a hearing apparatus 10, such as a wireless interface 25;

means 220 for communication with a server-side server of the system for example with an FTP or Internet connection via a telecommunication network;

a user application 203 loaded in a memory 202 and managed by a processor 201;

The server side of the system comprises at least:

a server-side server 300, for example a virtual server on a cloud in a telecommunications network, provided with:

means 320 for communication with a user-side multimedia device, means for analysis of telemetric data relating to current operation of the acoustic device;

means for analysis of diagnostic data relating to current operation of the acoustic device;

means for processing a new set of configuration data of the hearing apparatus 10 on the basis of telemetric data and diagnostic data for current operation of the device;

the server-side server must also have available the current configuration data of the operating parameters of the hearing apparatus (i.e. the current configuration profile).

The analysis and processing means may comprise a processor with suitable loaded programs for performing analysis and processing by means of an operator or automatically using pre-programmed procedures.

With reference now to FIG. 2, a hearing apparatus 10 illustrated by way of example and particularly well suited for adjustment using a process according to the invention comprises:

- a processing and control processor 10a, in the example a microprocessor;
- at least one memory, in the example shown a RAM 16; the RAM 16 contains a set of data forming a configuration profile of the apparatus, on the basis of which the processor 10a adjusts the different parameters for adjusting operation of the apparatus;
- a first microphone 11a and a second microphone 11b;
- an analog/digital converter ADC for the signals originating from microphones 11a, 11b;
- a block 12 for managing a microphone recording configuration. The block 12 processes the signals emitted by the two microphones 11a,11b so as to obtain at its output a combined audio signal s12 which emulates an audio signal acquired with a predefined microphone recording configuration: in particular, the block 12 may emulate a recording configuration having a polar pattern, which is for example omnidirectional, unidirectional (e.g. cardioid, hypercardioid), bidirectional or directional with variable focusing. Moreover, the microphone configuration block 12 may in general be set for a fixed microphone configuration, which may be varied only manually by a user or operator, or a variable microphone configuration, which may be varied automatically by the microprocessor depending on different parameters recorded;
- a block 13 for preliminary management of the audio signal emitted by the block 12, the block 13, referred to in the language of the sector as Speech/Noise Manager, carries out a preliminary analysis and pre-processing in terms of Signal/Noise ratio of the input signal s12; in particular the manager block 13 performs the following operations:
  analyses 13a the input signal s12 identifying—using pre-programmed criteria, for example on the basis of the frequency, waveform and a comparison with pre-defined patterns—at least three signal components, each of which carries a certain type of signal:
  a component s13v which carries respective components of the signal s12 identified as voice type signals (with harmonics and patterns typical of spoken language);
  a component s13M which carries respective components of the signal s12 identified as music type signals;
  a component s13N which carries respective components of the signal s12 identified as noise;
  records 13b an amplitude (or power) level A13V,A13M, A13N of each analysed component s13V,s13M,s13N of the input signal s12;
  compares 13b the amplitude levels A13V,A13M of the components identified as useful signal with the components A13N identified as noise;
  if the ratio A13V/A13N; A13M/A13N; A13V+A13M/A13N between the amplitude of the voice and/or music signal components s13V,s13M and the amplitude of the noise components s13N is lower than a pre-programmed threshold, the manager block 13 intervenes 13b1 attenuating the amplitude of the noise component s13N down to a maximum threshold value I13b (that is also a configuration parameter included in the configuration profile of the apparatus), obtaining an attenuated noise component s13N (in the case of speech and noise the noise is reduced, in the case of music and noise the noise is reduced, in the case of voice, music and noise only the noise is reduced, so as to avoid altering the volume ratio between the music and voice in a song);
  recombines the at least three components s13V,s13M, s13N, providing at its output a signal s13.

According to a preferred aspect of the invention it is envisaged that in the block 13 the apparatus 10 is designed to acquire current telemetric data representative of the acoustic environment in which the apparatus is operating, in particular identifying some characteristics of at least one signal input to the hearing aid, and of the processing performed by the apparatus 10 in response to the at least one input signal and therefore said acoustic environment; as will become clearer below, this data will allow in an innovative manner calibration/adjustment procedures to be performed remotely. According to the preferred embodiment shown, the amplitude (power) level values A13V,A13M,A13N recorded for each component s13V, s13M, s13N by the manager 13, and/or a useful Signal/Noise ratio value $S/N_{out}$ of the signal s13 output by the block 13, following the action taken by the manager 13 and/or an action level I13b currently applied by the manager 13, are acquired. The telemetric data acquired may be saved in one or more registers 16a of the memory 16;

- a block 14 for distributing the signal s13 emitted by the manager 13 over different frequency channels (for example up to 48 channels), for example by means of passband filtering of the input signal s13 so as to provide at the output n signals $s14_1, s14_2, \ldots, s14_n$ distributed over corresponding n frequency channels Ch1, . . . ,Chn;
- a block 15 for processing each channel Ch1, . . . ,Chn, independently of each other; in particular, the block has at least one element $15_1, 15_2, \ldots, 15n$ for adjusting the gains of each channel; as shown in FIG. 2, the element $15_1, 15_2, 15n$ for adjusting the gains of each channel is preferably provided with at least three amplifiers/attenuators $15_1G40, 15_1G60, 15_1G90$ in parallel, for adjusting the gain of sounds of the respective channel divided up into at least three amplitude (power) levels, for example low amplitude level gain G40 (30-40 db), medium amplitude level gain G60 (40-60 db) and high amplitude level gain G90 (60-90 db); optionally, downstream of the channel gain adjustment element 151, an automatic gain controller (AGC) $15GC_1$ may be provided for limiting the overall gain output by the single channel;
  downstream of the independent processor for each channel 15, the processed signals $s15_i$ of all the channels are recombined 15b and output s15 towards an automatic controller AGC-O of the overall output gain of the signal s15;
- a digital/analog converter DAC for converting the output signal s15 and at least one loudspeaker 19 for transmission, in the auditory canal, of the audio signal output by the hearing apparatus 10;
- wireless communication means 18 for connection to the multimedia device 200, for example of the Bluetooth, NFC or similar type;
- power supply means 17.

According to a preferred embodiment, the hearing apparatus is designed to acquire at least the following current telemetric data:
  configuration data for the microphone mode currently used by the hearing apparatus (e.g. omnidirectional, unidirectional (e.g. cardioid or hypercardioid), bidirectional, directional with variable focussing);

data representative of the action performed currently (namely contestually with the presence of the hearing problem) by the Speech/Noise manager 13, for example a value of the current ratio $S/N_{out}$ between useful signal and noise of the signal output by the manager block 13, or a level of action currently applied by the manager 13 to a component of the input signal;

data relating to the current amplitude level A13V of the voice audio component of the signal input to the manager block 13;

data relating to the current amplitude level A13M of the music audio component of the signal input to the manager block 13;

data relating to the current amplitude level A13N of the noise component of the input signal.

The current telemetric data is acquired and/or saved by the processor 10a as an average over a predetermined time period, for example during the last minute of use, of the respective instantaneous recordings; by averaging, as described above, the current telemetric data, the transient noise in the acoustic environment in which the hearing aid is operating is at least partially filtered, and the current telemetric data thus acquired/saved may be better correlated with the diagnostic data.

The acquisition of the telemetric data may be performed continuously, at regular intervals and/or upon request/command of the processor of the hearing aid, preferably following a request/command sent from the multimedia device 200, activated by the user U.

In fact for the process according to the invention only current telemetric data acquired following a request/command sent from the multimedia device 200 to the hearing aid is required; as will become clearer below said data will be at least partially aligned temporarily with the operating defect or problem detected by the user and the corresponding diagnostic data.

Although illustrated by means of analog signal processing blocks, it is understood that in modern hearing aid apparatus the various blocks may generally be integrated in a single chip and realized in digital form via algorithms for digitally processing signals, programmed in the memory 16 and implemented by processing means (such as the control processor) also integrated in the same chip.

In addition, according to standard practices which are not described in detail, it is envisaged that the first calibration/adjustment (fitting) of the numerous adjustment parameters of the different functional blocks of the hearing apparatus (referred to overall as "configuration profile" or "operating parameter configuration") is preferably carried out on the basis of a hearing test or similar procedure performed at specialized laboratories. One object of the present invention is to provide innovative methods and systems which allow calibration or adjustment of the said operating parameters of the apparatus, after said initial configuration, without the need for the user to be physically present at a specialized laboratory. Based on the limited amount of current telemetric data representing the acoustic environment in which the hearing aid is operating and its operating behaviour in response thereto, acquired in accordance with the invention, it will be possible to implement procedures for remote adjustment of the hearing apparatus, as will become clearer below.

With the combination of elements described, the operating principle of the system is as follows:

the user U wearing the hearing apparatus 10 has a hearing problem and starts the user application 203 by means of a suitable interface of the multimedia device;

via the communication means 210 of the multimedia device, the user application requests from the hearing apparatus 10 the current telemetric data indicating characteristics of the acoustic environment in which the apparatus is operating and the operating behaviour of the said apparatus in response to said environment;

the microprocessor 10a acquires this current telemetric data which preferably comprises at least:

the at least three sets of data relating to the amplitude level A13V;A13M;A13N of the voice, music and noise components which are input;

one or more sets of data indicating the microphone mode currently emulated and in use in the microphone management block 12 of the apparatus, and the data representing the action currently performed by the Speech/Noise manager 13, in particular the value $S/N_{out}$ of the Signal (Voice and/or Music)/Noise ratio of the signal s13 output by the manager block 13 or the action level currently applied by the manager 13;

the telemetric data is for example saved in a file of the RAM memory 16 of the apparatus 10 and sent to the multimedia device which saves it in its own memory 202;

contestually the user application starts a tool for diagnosis of the current operation of the hearing aid in order to obtain diagnostic data for the current operation of the device; preferably, the diagnosis tool asks the use to enter objective information relating to one or more problems and/or defects affecting the current operation of the hearing aid 10 in the acoustic environment in which it is operating;

the diagnostic data of the current operation thus obtained is forwarded to the server-side server 300 via the communication interfaces 220;230, respectively, of the multimedia device 200 and the server 300;

the current telemetric data downloaded from the hearing apparatus is also forwarded to the server 300;

the current configuration data of the numerous operating parameters of the hearing apparatus are made available on the server-side server; preferably a set of current configuration data is also downloaded from the memory 16 of the hearing apparatus to the multimedia device 200 and, via the latter, sent to the server 300. However, it is also possible to provide a database on the server side with all the current configuration data of the apparatus of users subscribing to the service;

the server processes via suitable processing means a new set of configuration data on the basis of the diagnostic data and the current telemetric data received;

the new configuration data of the operating parameters is then sent to the multimedia device 200 which forwards it to the hearing device 10, for new configuration thereof;

the processor 10a of the apparatus 10 sets the new configuration data as current configuration data for the various parameters for adjusting operation of the apparatus;

if the new configuration is still not suitable for the user's needs, the procedure may be repeated using updated diagnostic data for the current operation and current telemetric data, acquired following a new request/command sent by the device 200.

According to a first preferred embodiment, said objective diagnostic data for current operation of the hearing device and/or operation perceived by the user comprises:

I) a first set I of diagnostic data identifying at least one operating problem (encountered by the use) with the current configuration profile of the operating parameters of the apparatus.

The diagnosis tool of the user application of the multimedia device 200 will be programmed to acquire the said first set of data relating to the type of problem encountered.

With reference to a user interface 203a shown by way of example in FIG. 4, the diagnosis tool preferably asks the user to enter the information as to the type of problem encountered; in particular, the user is asked to choose a type of problem from among a limited number of types of problem pre-programmed in the application; preferably said limited number of types of problem comprises a plurality of possible choices, each associated in the adjustment system (at the time of entry by the user and saving or subsequently for example by the analysis means of the server 300) with one of the following objective types of problem:

Problem of discomfort perceived for a type of acoustic signal;
Problem of an excessively high volume of a type of acoustic signal;
Problem of an excessively low volume of a type of acoustic signal;
Problem of incomprehensibility of a type of acoustic signal;
Problem of substantial non-detection of a type of acoustic signal.

For easier interaction with the user, this first set of diagnostic data may be acquired by displaying a selection interface 203aI comprising for example the following examples of choices as to the type of problem: "I feel discomfort", "I hear too high", "I hear too low", "I am unable to understand", "I cannot hear", as said, each choice is associated by the system with one of the objective types of problem defined above.

The first diagnostic data is saved in a file in the memory 202 of the multimedia device. According to a preferred aspect of the invention, in the adjustment system each type of problem is in turn associated—by the user application at the time of acquisition of the data or subsequently by the analysis means of the server 300—with one of the following categories of problem:

problems relating to a single sound source;
problems relating to at least two sound sources.

Then the diagnostic tool acquires:

II) a second set of data identifying the type of acoustic signal for which there is the problem identified by the first set of diagnostic data.

Preferably, the second set of diagnostic data comprises data identifying the type of signal which is affected by the problem identified by the first set of data. The type of signal is preferably chosen from among a set of types of signals each of which may be attributed to and, as will become clear below, associated by the adjustment system with one of the following objective macro-categories of signal:

Voice audio signals;
Music audio signals;
Noise audio signals;

Preferably, the interface 203aII of the diagnosis tool offers the user U the choice from among the following:

Voice audio signals: a voice of someone speaking to me, my own voice, a voice on the phone, a voice on the TV/radio/computer.
Music audio signals; live music, music on a TV/radio/computer;
Noise audio signals; the noise of my car, the noise of traffic, the noise of a household appliance;
audio signals of the noise type from an artificial source: the ringing of a telephone/mobile device, the sound of the doorbell/intercom system, the timer of a household appliance.

It is also preferably possible to choose a generic audio signal, by selecting "a sound in general" which is associated with the objective macro-category of noise.

According to a further preferred embodiment, it is possible to acquire 203aIII:

III) a third set of diagnostic data identifying at least one direction of origin of said audio signal in relation to which there exists the objective problem identified by the set I of diagnostic data.

According to a further preferred embodiment, it is possible to acquire:

IV) a fourth set of diagnostic data, identifying at least one disturbing audio signal which is superimposed on the audio signal for which the problem identified by the first set of diagnostic data was detected; the disturbing audio signal can be preferably attributed to and associated by the adjustment system with one of the said objective macro-categories of signal defined above for the second set of diagnostic data (voice, music and noise).

Preferably, the fourth set of data is acquired only if the first set of data identifies an objective problem relating to more than one sound source, in particular a problem of incomprehensibility of a type of acoustic signal; in this way it is possible to acquire diagnostic data relating to the type of noise which disturbs the comprehensibility of the audio signal identified by the second set of diagnostic data. Preferred examples of possible choices proposed to the user by a preferred diagnostic tool for acquisition of the set IV of diagnostic data comprise the following: live music, music on a TV/radio/computer, the noise of a lot of people talking, the noise of my car, the noise of traffic, the noise of a household appliance, the ringing of a telephone/mobile device, the sound of the doorbell/intercom system, a sound in general.

According to a preferred embodiment, when the fourth set of data is acquired, it is also possible to acquire:

a fifth set of diagnostic data identifying at least one direction of origin of said audio signal disturbing the audio signal in relation to which there is problem.

The application then saves all the sets of diagnostic data acquired in one or more files in a memory of the multimedia device; then the device forwards (e.g. upon a user command 203aS) the files to the server 300, for processing of a new set of data for a new configuration of the operating parameters.

Preferably, the user application and/or the server 300 assign the amplitude level A13V,A13M,A13N of the input signal components s13V,s13M,s13N indicated in the current telemetric data to one of three or more adjustment macro-levels, for example low level, medium level and high level, defined correspondingly to the channel gain adjustment levels $15_fG40,15_fG60,15_fG90$ which can be configured for each channel Ch1, . . . ,Chn by means of respective configuration parameters.

Upon command, for example a confirmation entered by means of the user application, the at least one file of current telemetric data is sent via the communication means of the multimedia device to the system server, for analysis and processing of a new configuration of the operating parameters. Once the current telemetric data and the diagnostic data acquired have been received by the server 300, which has available the current configuration (fitting) data of the hearing apparatus 10, it is possible to process, on the server side of the system, a new configuration profile of the hearing aid, adjusting at least one operating parameter on the basis of an analysis of the diagnostic data cross-analysed/correlated with the current telemetric data acquired.

An example of embodiment shown in FIG. 4 shows a server side in which processing of the new configuration profile is performed by a specialized operator who processes a new configuration profile by means of a telematic station connected—locally or also remotely—to the server 300.

However, it is envisaged that the new configuration data is preferably processed by means of an automatic adjustment procedure, for example programmed on the server 300.

In greater detail, it is possible to implement a process for adjusting one or more operating parameters of the hearing apparatus in accordance with the following steps:

1) analysis of the objective information of the current diagnostic data, for example the first and second sets of diagnostic data, in order to identify the type of problem of the current configuration of the apparatus and the type of audio signal in relation to which the identified problem is present;

1.1) if the diagnostic data identifies a problem relating to an audio signal originating from a single sound source, preferably the current telemetric data is analysed and, if said data indicates that the three voice, music and noise components s13V,s13M,s13N of the audio signal s13 input to the Speech/Noise manager block 13 have an amplitude A13V, A13M,A13N comprised within different macro-levels (e.g. low (G40), medium (G60) or high (G90)), the current configuration parameters are varied by modifying the gain/compression levels of each channel Ch1, . . . ,Chn in a manner consistent with the type of problem and the type of signal identified by the diagnostic data and with the current levels identified by the telemetric data. This preferred mode of implementation of an adjustment is particularly simple and rapid, but not always reliable, since it is based on the assumption that if the diagnostic data entered by the user indicates a problem relating to an audio signal associated with a single sound source, the parameters relating to the microphone configuration and the action taken by the Speech/Noise manager do not require adjustment. This is generally applicable, but there are rare cases where a particularly macroscopic initial adjustment defect may determine that these parameters also require adjustment.

According to a further preferred mode of implementation, the processing, of new configuration data involves carrying out on the current configuration parameters only the first or each possible action from among the following actions 1.1a, 1.1b and 1.1c:

1.1a) Microphone Mode Configuration

If the diagnostic data correlated with the current telemetric data indicates that the audio signal relative to the identified problem originates from a direction (e.g. identified by the third set of diagnostic data) not consistent with the currently configured microphone mode indicated by the respective current telemetric data acquired, in particular a direction not included in the polar pattern of the microphone mode currently configured by the configuration profile: modifying the currently configured microphone mode in a consistent manner, for example so that the polar pattern emulated by the new microphone mode includes the direction of origin of said audio signal to which the identified problem is related;

if the audio signal, to which the identified problem relates, originates from a direction consistent with the current operating configuration of the microphone or if it is intended to carry out each possible adjustment action: passing to the next step 1.1b.

1.1b) Channel Gain Configuration if the current telemetric data indicates that the three voice, music and noise components s13V,s13M,s13N of the audio signal s13 input to the Speech/Noise manager block 13 have an amplitude A13V,A13M,A13N comprised within different macro-levels (e.g. low (G40), medium (G60) or high (G90)): varying the current configuration parameters by modifying the gain/compression (macro) levels (e.g. low (G40), medium (G60) or high (G90)) of the channels Ch1, . . . , Chn in a manner consistent with the type of problem and the type of signal identified by the diagnostic data and with the current levels identified by the telemetric data;

if the current telemetric data indicates that the voice and/or music components s13V,s13M and the noise component s13N of the audio signal s12 input to the Speech/Noise manager block 13 have an amplitude comprised within similar amplitude levels (or if the telemetric data A13V,A13M,A13N indicates a value attributable to a same adjustment macro-level) or if it is intended to carry out each possible adjustment action: passing to the next step 1.1c).

1.1c) Speech/Noise Manager Configuration

Modifying at least one adjustment parameter of the action configuration of the Speech/Noise manager block 13 in a manner consistent with the type of problem and the type of signal identified by the diagnostic data; preferably the value of the parameter relating to the level of action of the Speech/Noise manager 13 is modified: for example, if the diagnostic data indicates a problem of too much noise and too low voice and the telemetric data indicates that the currently configured level of action is not the maximum possible, the level of action is increased; if instead the diagnostic data indicates a low sound (for example for an audio signal such as the sound of a bell) in the presence of voice and the telemetric data indicates that the level of action currently configured is not the minimum possible, the level of action of the manager 13 is reduced.

1.2) If the diagnostic data identifies—for example by means of the first, second and fourth set of diagnostic data—a problem relating to two or more sound sources: carrying out only the first or each action possible on the configuration parameters from among the following actions 1.2a, 1.2b1.2c.

1.2a) Microphone Mode Configuration

If the directions of origin indicated by the diagnostic data for the signal to which the problem is relative (e.g. sets II and of diagnostic data) and for the further disturbing signal (sets IV and V of diagnostic data) are different directions:

if the audio signal relative to the problem (identified by the second set of data) originates from a direction (set III of diagnostic data) not consistent with the current operating configuration of the microphone indicated by the respective current telemetric data: modifying the setting of the microphone management block in a manner consistent with the problem and the directions of origin indicated by the diagnostic data, for example so that the polar pattern emulated by the microphone management block 12 includes the direction of origin of the audio signal (set II of diagnostic data) to which the problem is relative (set III of diagnostic data), but not with that (set V of data) of the further disturbing signal (set IV of data);

if the audio signal relative to the problem (identified by the set II of data) originates from a direction (set III of data) not consistent with the current operating configuration of the microphone, indicated by the respective current telemetric data, or if it is intended to carry out each possible adjustment action: passing to the next step 1.2b.

1.2b) Channel Gain Configuration

If the current telemetric data shows different amplitude levels (low, medium, high) for the components (Voice, Music, Noise) of the signal input to the Speech/Noise manager 13 with which the following may be respectively assimilated:

the signal macro-category to which the input audio signal (set II of diagnostic data) relative to the hearing problem is attributable; and the signal macro-category to which the further input audio signal is attributable (set IV of diagnostic data);

then in this case the configuration parameters for the level compression/gain of the channels Ch1, . . . ,Chn are modified in a manner consistent with the current telemetric data and diagnostic data acquired; since the signal associated with the problem indicated by the diagnostic data has an amplitude (known from the current telemetric data) comprised within one of the adjustment macro-levels, e.g. low G40, medium G60 or high G90, depending on the type of problem indicated it is possible to increase or decrease the gain of the corresponding macro-level on each channel Ch1, . . . ,Chn.

EXAMPLE

I and II diagnostic data indicate: "the traffic noise disturbs me"

the telemetric data indicates an input amplitude level of the components: Noise=82 dB, Voice=28 dB, Music=23 dB variation of the configuration profile to be performed: reduction of the high macro-level adjustment G90 gain on all the channels Ch1, . . . ,Chn.

If the current telemetric data indicates instead an amplitude comprised within similar amplitude levels (low, medium, high) for the two components of the input audio signal defined above (component to which the problem is relative and disturbing component), or if it is intended to perform each adjustment action possible: passing to the next step 1.2c.

1.2c) Speech and Noise Manager Configuration

If the current telemetric data indicates similar amplitude levels (low, medium, high) for the components (Voice, Music, Noise) of the signal input to the Speech/Noise manager 13 with which the following may be respectively assimilated:

the signal macro-category with which the input audio signal relative to the hearing problem is associated (set II diagnostic data); and the signal macro-category with which the further input audio signal is associated (set IV of diagnostic data);

then action is taken by varying the adjustment parameters of the Speech/Noise manager 13 in a consistent manner; preferably the value of the parameter relating to the level of action of the Speech/Noise manager 13 is modified: for example, if the diagnostic data indicates a problem of noise which is too loud and voice which is too low and the telemetric data indicates that the currently configured level of action is not the maximum possible, the level of action is increased; if instead the diagnostic data indicates a low sound problem (audio signal such as a doorbell) in the presence of voice and the telemetric data indicates that the level of action currently configured is not the minimum possible, the level of action configured is reduced.

In connection with these examples of adjustment procedures according to the invention, it is advantageous to perform only the first possible action if simpler processing from a computational point of view is required, it being possible if necessary to improve this adjustment with a subsequent adjustment cycle after the user has tested the new configuration in the environment in which the problem was detected; if instead it is decided to perform each possible action, the new configuration will be better adjusted immediately, albeit with a small increase in the computational processing load.

Example 1

The server 300 receives from the multimedia device the following current telemetric data acquired from the hearing aid 10 and diagnostic data collected by the multimedia device 200:

Telemetric Data:
Input Voice amplitude: 61 dB;
Input Noise amplitude: 42 dB;
Input Music amplitude: 23 dB;
Active Microphone Configuration: automatic directional;
S/N Manager level: 1 out of 7 (where 7 indicates for example 21 dB)

Diagnostic Data:
First data set (I): "I hear too low"
Second data set (II): "ringing of mobile phone"
Third data set (III): "in front of me"
Fourth and fifth data sets (IV, V): not present Variation of the Configuration Parameters:
Applying the preferred remote adjustment procedure the server 300 carries out the following operations:
analysis of the data set s I and II in order to identify the type of problem and the type of audio signal affected by the problem identified; the problem identified consists of a problem of too low volume of an artificial-sound audio signal (attributable to and associated with the noise category of the telemetric data); it is therefore a problem relating to an audio signal of a single sound source.

The diagnostic data set III indicates that the audio signal affected by the identified problem originates from a direction consistent with the currently configured microphone configuration, and therefore the microphone configuration is not modified;

the current telemetric data indicates that the three components (voice, music, noise) of the audio signal s13 input to the Speech/Noise manager block 13 are on different amplitude levels (Voice=61 dB, Music=23 dB, Noise=42 dB): the configuration parameters are therefore varied by modifying the gain/compression levels of all the channels Ch1, . . . ,Chn in a manner consistent with the type of problem and the type of signal identified by the diagnostic data; for example using the data of Example 1, the gain of the macro-level G40 (gain of the amplitudes in the region of 40 dB) of each channel Ch1, . . . ,Chn is increased, applying for example an initial increase of 3 dB.

The new configuration profile is sent from the server 300 to the multimedia device 200 and sent from the latter to the hearing aid which saves it in the memory 16;

The microprocessor of the hearing aid 10 sets the new configuration profile as active (or default) profile.

In Example 1 the hearing apparatus receives at its input a voice component and a music component as well as the ringing of a mobile phone which can be assimilated with a noise component (i.e. deducible from the analysis of the current telemetric data); the S/N manager 13 cannot act since its function is to increase the voice level and reduce the noise, and its level of action is already minimal in the current configuration and therefore the S/N manager cannot cancel out ringing of the mobile phone, the amplitude of mobile phone ringing is however comprised within the volume level which can be adjusted by the amplification control G40: by modifying the amplification parameter of the level G40 of all the channels it is therefore possible to increase the amplification of ringing of the mobile phone without modifying in any way the voice, since the diagnostic data entered by the user does not indicate that it is annoying or a disturbance (reducing it in this case would "shift" the problem, allowing ringing of a mobile phone to be more audible, but in another situation the user could have difficult hearing a voice which is not audible enough).

It is therefore clear how, with a process and architecture according to the invention, it is possible to perform easy remote adjustment of the parameters for adjusting the operation of the hearing aid by means of a system comprising a multimedia device on the user side able to communicate with the hearing aid and with a server for creating a new configuration profile of the operating parameters on the basis of an analysis of the telemetric data acquired by the hearing aid cross-analysed with objective diagnostic data acquired by means of the multimedia device.

It is therefore clear how, with the system and the method for remote adjustment according to the invention, it is possible to collect objective telemetric and diagnostic data representative of the acoustic environment in which the problem occurs and of the problem itself (differently from the situation where the hearing aid user has to visit a specialized centre in order to consult a hearing aid specialist and would be able to describe the acoustic environment in which the problem occurred based only his/her recollections); in this way the system is able to operate with real and objective informations which are at least partially aligned temporarily with each other as well as with the hearing problem and/or operating defect detected by the user. The method and the system also offer the opportunity of testing immediately a new adjustment in the environment in which the problem occurred. In addition, lost time is eliminated owing to the possibility of remote adjustment independently of the physical distance between specialist and user. Even if the new adjustment is performed by technical experts, the system nevertheless offers the client the opportunity for a round-the-clock service by making use of different experts working in different countries owing to time zone differences. In addition, with the hearing aid and the process according to the invention, it is possible to develop an automatic adjustment procedure which may also make use of the data stored in the cloud server 300, being based also on positive adjustment results obtained over the course of time with a consequent increase in the degree of satisfaction of the end user who is no longer dependent on the technical expert.

According to a further preferred mode of implementation, in the case of a fixed directional microphone setting, i.e. in the case where it is not possible to activate the automatic microphone function, for example because the hearing apparatus is not equipped with this function or because the automatic system generates confusion for the hearing aid user, the variation in configuration of the microphone mode described under points 1.1a or 1.2a may comprise the following steps:

creation of a configuration profile in which the adjustment parameters of the microphone setting are varied in a manner consistent with the telemetric data and/or the diagnostic data acquired.

The profile may be loaded in the RAM 16 of the apparatus and activated in one or more of the following ways:

According to a first option it is possible to activate manually the configuration profile loaded in the RAM 16 by means of a special function of the multimedia device which, upon command of the user, sends an instruction to the processor 10*a* for manual activation of the loaded profile; the manual command may be deactivated subsequently and reactivated selectively in environments similar to that for which the adjustment profile was requested and generated;

according to a further implementation option it is possible to detect by means of a GPS tracker of the multimedia device (commonly present in modern smartphones) data for geographical location of the position of apparatus user; the multimedia device may also be designed to send automatically an instruction to the processor 10*a* for activation of the loaded profile, when the multimedia device detects by means of its own geographical tracker that the user is in the position (or close to the position) where the configuration profile was created or requested.

Example 2

The server 300 receives from the multimedia device the following telemetric data acquired from the hearing aid 10 and diagnostic data collected by the multimedia device 200:

Telemetric Data:

Voice amplitude: 67 dB, Noise amplitude 71 dB, Music amplitude 0 dB, active microphone mode: automatic directional, S/N manager action level: 2 out of 7

Diagnostic Data:

First data set (I): "I can't understand"

Second data set (II): "the voice of someone speaking to me"

Third data set (III): "in front of me"

Fourth data set (IV): "the noise of many voices"

Fifth data set (V): "behind me"

Variation of the Configuration Parameters:

Since the diagnostic data indicates a problem relating to several sound sources (diagnostic data sets I, II, IV) and the directions of origin indicated by the diagnostic data for the signal affected by the problem (diagnostic data set III) and for the further signal (diagnostic data set V) are different directions, the processing means of a new configuration profile, considering the active microphone configuration, indicated by the associated telemetric data, modify the configuration parameters of the microphone management block in a manner consistent with the problem and the directions of origin indicated by the diagnostic data.

The new configuration profile will have for example a fixed (not automatic) directional microphone setting with polar pattern which excludes the region situated behind the hearing aid user.

The new configuration profile is sent to the multimedia device 200 which forwards it to the hearing aid 10 where it is saved in the RAM 16;

according to the preferred mode of implementation described above, the new configuration profile may be activated manually by the user by means of control of the user application which sends a command to the microprocessor 10a of the hearing aid for activation of the loaded configuration profile;

in addition or alternatively the user application may detect a GPS position and automatically send the activation command to the hearing aid when the user is in the vicinity of the detected position.

It is therefore clear how, with the preferred mode of implementation of the process described above, also in the case of a fixed microphone configuration it is possible to load a specific configuration profile for such circumstances which may be activated by the user as required, or automatically, by means of the multimedia device 200.

Although described in connection with a number of embodiments and a number of preferred examples of embodiment of the invention, it is understood that the scope of protection of the present patent is determined solely by the claims below.

The invention claimed is:

1. Process for remotely adjusting a hearing aid worn by a user,
   comprising the following steps:
   acquiring from the hearing aid (10) telemetric data representative of the acoustic environment in which the hearing aid is operating and of the operative behaviour of the hearing aid (10) in response to this environment,
   downloading said telemetric data from the hearing aid to a user-side multimedia device (200) of a remote adjustment system;
   acquiring by means of the multimedia device (200) diagnostic data for the current operation of the hearing aid, which is entered by the user and saved in the multimedia device (200);
   forwarding the diagnostic data saved in the multimedia device (200) to a server-side server (300) of the remote adjustment system;
   forwarding the telemetric data downloaded from the hearing aid from the multimedia device (200) to the server (300);
   providing current configuration data for operating parameters of the hearing aid to the server-side server;
   wherein
   the telemetric data acquired and forwarded to the server (300) comprises current telemetric data acquired from the hearing aid (10) following a request/command sent from the multimedia device (200) to the hearing aid (10) and acquired and/or saved as an average of respective instantaneous recordings over a predefined time interval;
   during acquisition of the said diagnostic data the user is requested to enter information relating to one or more hearing problems and/or defects relating to the current operation of the hearing aid (10) in the acoustic environment in which the hearing aid is operating with the current configuration of the operating parameters, and
   said information is saved in at least a first set (I) of said diagnostic data and forwarded from the multimedia device (200) to the server (300);
   and said information entered by the user is associated in the adjustment system with objective diagnostic information relating to the current operation of the hearing aid in the acoustic environment in which it is operating;
   the process comprises a step of processing on the server side new configuration data of the operating parameters of the hearing aid, by adjusting at least one parameter of the current configuration on the basis of an analysis of the objective diagnostic information associated with the current diagnostic data received, correlated with an analysis of the current telemetric data received;
   wherein the process comprises the further steps of:
   sending the new configuration data of the hearing aid (10) to the multimedia device (200);
   forwarding the new configuration data from the multimedia device (200) to the hearing aid (10), for a new configuration thereof.

2. Process according to claim 1, wherein, for acquisition of a first set (I) of diagnostic data, the user is requested to choose a type of hearing problem from among a limited number of possible predefined choices and wherein each choice is associated in the adjustment system with one of the following objective types of problem:
   problem of discomfort perceived for a type of acoustic signal;
   problem of excessively high volume for a type of acoustic signal;
   problem of excessively low volume for a type of acoustic signal;
   problem of incomprehensibility of a type of acoustic signal;
   problem of substantial non-detection of a type of acoustic signal.

3. Process according to claim 1, wherein each type of problem is associated with one of the following objective categories of problem:
   problems relative to a single sound source;
   problems relative to at least two sound sources;
   and wherein said association is performed at the time of acquisition of the data or subsequently during analysis of the diagnostic data on the server side.

4. Process according to claim 1, wherein acquisition of diagnostic data comprises the acquisition of a second set (II) of data indicating the type of acoustic signal for which there exists the problem identified by the first set (I) of diagnostic data and wherein the type of signal is selected from a set of pre-programmed choices each associated in the adjustment system with one of the following objective macro categories of signal:
   voice audio signals;
   music audio signals;
   noise audio signals.

5. Process according to claim 1, wherein the acquisition of diagnostic data comprises the acquisition of a third set (III) of diagnostic data indicating at least one direction of origin of said audio signal to which the problem is relative.

6. Process according to claim 1, wherein the acquisition of diagnostic data comprises the acquisition of a fourth set (IV) of diagnostic data indicating the type of at least one disturbing audio signal which disturbs the audio signal for which there exists the problem identified by the first set of diagnostic data and wherein the disturbing audio signal is associated with one of said objective macro categories of signal defined for the second set of diagnostic data.

7. Process according to claim 6, wherein the fourth set and/or fifth set of diagnostic data is/are acquired only if the first set of data indentifies a problem relating to more than one sound source, preferably a problem of incomprehensibility of a type of acoustic signal.

8. Process according to claim 1, wherein the acquisition of diagnostic data comprises the acquisition of a fifth set of diagnostic data identifying at least one direction of origin of said disturbing signal.

9. Process according to claim 1, wherein the current telemetric data comprises data indicating a microphone configuration currently in use in the hearing apparatus, more particularly a microphone mode currently emulated by a block (12) managing the microphone detection configuration of the hearing aid (10).

10. Process according to claim 1, wherein the current telemetric data comprises:
  data relating to the current amplitude level (A13V) of a voice audio component (s13V) of a signal input to the Speech/Noise manager (13) of the hearing aid (10);
  data relating to the current amplitude level (A13M) of a music audio component (s13M) of the signal input to the Speech/Noise manager (13);
  data relating to the current amplitude level (A13N) of a noise component (s13N) of the signal input to the Speech/Noise manager (13);
and wherein each amplitude level (A13V,A13M,A13N) of each component (s13V,s13M,s13N) indicated by the telemetric data is associated with one of three or more adjustment macro-levels defined in accordance with gain adjustment levels (15$_i$G40,15$_i$G60,15$_i$G90) which can be configured for each channel (Ch1, . . . ,Chn) of the hearing aid by means of a respective configuration data for respective operating parameters.

11. Process according to claim 1, wherein the provision of the current configuration data to the server side is performed by downloading a current configuration profile of the operating parameters from the hearing aid to the multimedia device (200) and forwarding said current configuration profile from the multimedia device (200) to the server-side server; or
  by providing on the server side a data bank including the current configuration profile of operating parameters of the hearing aid.

12. Process according to claim 1, wherein the step of processing a new configuration profile comprises a step of analysis of the diagnostic data for identifying the type of problem of the current configuration profile and the type of audio signal to which the problem identified is relative;
  and wherein, if the diagnostic data identifies a problem relating to an audio signal originating from a single sound source and if an analysis of the current telemetric data indicates that the voice, music and noise components (s13V,s13M,s13N) of the audio signal (s12) input to the Speech/Noise manager block (13) have amplitudes (A13V,A13M,A13N) comprised within different adjustment macro levels, during processing of a new configuration at least one current configuration parameter is varied by modifying the adjustment macro-levels (G40;G60;G90) of the channels gain (Ch1, . . . , Chn).

13. Process according to claim 12, wherein, if the diagnostic data identifies a problem relating to an audio signal originating from a single sound source and
  if the current telemetric data indicates that the voice, music and noise components (s13V,s13M,s13N) of the audio signal (s12) input to the Speech/Noise manager block (13) have amplitudes associated with similar adjustment macro-levels, during processing of a new configuration at least one current configuration parameter from among the parameters for action of the Speech/Noise manager block (13) is modified in a manner consistent with the type of problem and the type of signal identified by the diagnostic data.

14. Process according to claim 12, wherein:
if the diagnostic data indicates a problem relating to two or more sound sources and if the directions of origin indicated by the diagnostic data for the signal relative to the problem and for one or more signals of the further sound sources are different directions and the current microphone mode indicated by the telemetric data is not consistent with the direction of origin of the audio signal related to the problem indicated by the diagnostic data and/or with the direction of a further audio signal indicated by the diagnostic data:
  during processing of new configuration data at least one control parameter of the currently configured microphone mode is modified in a manner consistent with the problem, the signal types and the directions of origin indicated by the diagnostic data.

15. Process according to claim 12, wherein:
if the diagnostic data indicates a problem relating to two or more sound sources and
  if the telemetric data indicates different amplitude levels (A13V,A13M,A13N) for the components (s13V,s13M,s13N) of the signal input to the Speech/Noise manager (13) with which the following may be respectively assimilated:
the objective macro-category of signal with which the audio signal relative to the hearing problem is associated and
the objective macro-category of signal with which the at least one further disturbing audio signal is associated:
  during processing of new configuration data at least one current configuration parameter relating to the level gain of the channels (Ch1, . . . , Chn) is modified in a manner consistent with the telemetric data detected and the diagnostic data acquired.

16. Process according to claim 12 wherein, if the diagnostic data indicates a problem relating to two or more sound sources and
  if the telemetric data indicates similar amplitude levels for the components (s13V,s13M,s13N) of the signal input to the Speech/Noise manager (13) with which the following may be respectively assimilated:
the objective macro-category of signal with which the audio signal relative to the hearing problem is associated; and
the objective macro-category of signal with which the at least one further disturbing audio signal is associated:
  during processing of new configuration data at least one current configuration parameter relating to the action of the Speech/Noise manager (13) is modified in a consistent manner.

17. Process according to claim 16, wherein a modification of the current microphone mode comprises a variation of the configuration profile such that the polar pattern emulated by the microphone management block (12) includes a direction of origin of the audio signal to which the problem is relative, but not a direction of origin of an audio signal which disturbs said signal related to the problem.

18. Process according to claim 1, wherein the step of processing a new configuration profile comprises the following steps:

a) analysis of the diagnostic data in order to identify the type of problem of the current configuration profile and the type of audio signal affected by the identified problem; and wherein, if the diagnostic data identifies a problem relating to an audio signal originating from a single sound source and indicates that the audio signal relative to the identified problem originates from a direction which is not consistent with the currently configured microphone mode indicated by respective telemetric data, during processing of a new configuration the currently configured microphone mode is modified.

19. Architecture according to claim 1, wherein the following current telemetric data is acquired from the hearing aid:
   data relating to the current amplitude level (A13V) of a voice audio component (s13V) of the signal input to a Speech/Noise manager (13);
   data relating to the current amplitude level (A13M) of a music audio component (s13M) of the signal input to the Speech/Noise manager (13);
   data relating to the current amplitude level (A13N) of a noise component (s13N) of the signal input to the Speech/Noise manager (13);
   and/or
   data representing an action currently performed by the Speech/Noise manager (13).

20. Architecture according to claim 1, wherein the diagnosis tool of the user application requests the user to choose the type of problem from among a limited number of possible pre-programmed choices and wherein each choice is assigned by the user application to one of the following objective types of problem:
   problem of discomfort perceived for a type of acoustic signal;
   problem of excessively high volume for a type of acoustic signal;
   problem of excessively low volume for a type of acoustic signal;
   problem of incomprehensibility of a type of acoustic signal;
   problem of substantial non-detection of a type of acoustic signal.

21. Architecture according to claim 1, wherein each type of problem is associated with one of the following objective categories of problem:
   problems relating to a single sound source;
   problems relating to at least two sound sources;
   and wherein said association is performed by the user application at the time of acquisition of the data or subsequently by the means for analysis of the diagnostic data of the server (300).

22. Architecture according to claim 21, wherein the multimedia device sends the current telemetric data and the diagnostic data to the server (300).

23. Architecture according to claim 1, wherein the user application acquires a fourth set (IV) of diagnostic data indicating at least one disturbing audio signal which disturbs the audio signal for which there exists the problem identified by the first set (I) of diagnostic data and wherein the disturbing audio signal is associated with one of said macro categories of signal defined for the second set of diagnostic data.

24. Architecture according to claim 23, wherein the fourth and/or fifth set(s) of diagnostic data is/are acquired only if the first set of data identifies a problem relating to more than one sound source, preferably a problem of incomprehensibility of a type of acoustic signal.

25. Architecture according to claim 1, wherein the user application acquires a fifth set of diagnostic data identifying at least one direction of origin of said disturbing audio signal.

26. Architecture according to claim 1, wherein the current telemetric data comprises:
   data relating to the current amplitude level (A13V) of a voice audio component (s13V) of the signal input to the Speech/Noise manager (13);
   data relating to the current amplitude level (A13M) of a music audio component (s13M) of the signal input to the Speech/Noise manager (13);
   data relating to the current amplitude level (A13N) of a noise component (s13N) of the signal input to the Speech/Noise manager (13);
and wherein the user application and/or the server (300) assign the amplitude level (A13V,A13M,A13N) of each component (s13V,s13M,s13N) indicated by the telemetric data to one of three or more adjustment macro-levels defined in accordance with gain adjustment levels ($15_iG40, 15_iG60, 15_iG90$) which can be configured for each channel (Ch1, . . . ,Chn) of the hearing aid.

27. Hearing aid architecture comprising:
   a hearing aid which comprises:
      a processing and control processor (10a),
      at least one memory (16), for saving a set of data forming a configuration profile of the hearing aid, on the basis of which the processor (10a) adjusts various parameters for controlling operation of the hearing aid;
      microphone transducer means (11a;11b);
      a block (12) for managing a microphone recording configuration, by processing audio signals emitted by the microphone transducer means (11a;11b) and outputting an audio signal (s12) which emulates an audio signal acquired with a microphone recording configuration defined on the basis of the current configuration profile;
      a Speech/Noise manager (13) for preliminary management of the audio signal emitted by the microphone management block (12), the manager (13) being designed to perform a preliminary analysis and pre-processing in terms of signal/noise ratio of the signal (s12) emitted by the microphone management block (12);
      a block (14) for distributing the signal (s13) emitted by the manager (13) over several frequency channels, so as to output a plurality (n) of signals (s141,s142, . . . ,s14n) distributed over corresponding (n) frequency channels (Ch1, . . . ,Chn);
      a block (15) for independently processing each channel (Ch1, . . . , Chn), comprising at least one element (151,152, . . . ,15n) for adjusting the gains of each channel;
   wherein downstream of the independent channel processor (15) the processed signals (s15i) of all the channels are recombined (15b) and transferred to an output (s15);
      at least one loudspeaker (19) for transmission, in the auditory canal of a user (U), of the audio signal output by the hearing aid (10);
      wireless communication means (18) for connection to a multimedia device (200);
   wherein the hearing aid (10) is designed to acquire and save in one or more registers (16a) of the memory the telemetric data representing the acoustic environment in which the hearing aid is operating, and/or indicating an operating behaviour of the hearing aid (10) in response to such environment, and wherein the processor (10*a*) is programmed to perform sending of said telemetric data to a user-side multimedia device (200);

a system for remote adjustment of a hearing aid, comprising:

a user-side multimedia device (200) which comprises:
means (210) for communication with the hearing aid (10);
means (220) for communication with a server (300) on a server side of the system;
a user application (203) loaded in a memory (202) and managed by a processor (201);
a server-side server (300) equipped with:
means (320) for communication with a user-side multimedia device,
means for analysis of telemetric data relating to the hearing aid;
means for analysis of diagnostic data relating to current operation of the hearing device;
means for processing a new set of configuration data of operating parameters of the hearing aid (10) on the basis of telemetric data;
wherein the multimedia device (200) is designed to download telemetric data from the hearing aid and forward it to the server (300) and wherein
the server (300) is also provided with a current configuration profile of the operating parameters of the hearing aid;
wherein the multimedia device sends the telemetric data and the diagnostic data to the server (300), wherein the hearing aid is adapted to acquire the current telemetric data following a request/command sent from the multimedia device (200) to the hearing aid (10) and the current telemetric data is acquired and/or saved as an average of respective instantaneous recordings over a predefined time interval;

the user application (203) of the device (200) comprises a tool for diagnosing the current operation of the hearing aid (10), designed to acquire diagnostic data of current operation of the hearing aid within the acoustic environment in which it is operating, and in that the diagnosis tool requests the user to enter information relating to one or more problems and/or defects affecting the current operation of the hearing aid (10) in the acoustic environment in which the hearing aid is operating, wherein the device (200) is configured to save said information in one or more diagnostic data sets and forward said one or more diagnostic data sets to the server (300);

the adjustment system associates said information entered by the user with objective diagnostic information relating to the current operation of the hearing aid in the acoustic environment in which it is operating; and the processing means of the server (300) are configured to process new configuration data of the operating parameters of the hearing aid, adjusting at least one parameter of the current configuration on the basis of an analysis of the objective diagnostic information associated with the current diagnostic data received, correlated with an analysis of the current telemetric data received, performed by the respective analysis means;

wherein:
the server (300) is configured to send the new configuration data of the hearing aid (10) to the multimedia device (200);
and the multimedia device (200) is configured to forward the new configuration data received to the hearing aid (10), for a new configuration thereof.

28. Architecture according to claim 27, wherein said telemetric data comprises data indicating the currently used microphone configuration of the hearing aid.

29. Architecture according to claim 27, wherein the current telemetric data is acquired and/or saved in the memory by the processor (10*a*) as an average over a predefined time period, in particular over the last minute of use, of respective instantaneous recordings.

30. Architecture according to claim 27, wherein said diagnostic data for the current operation of the hearing aid comprises a first set of diagnostic data indicating at least one hearing problem encountered by the user with a current configuration profile of the hearing aid.

31. Architecture according to claim 30, wherein the diagnosis tool acquires a second set (II) of data indicating the type of acoustic signal for which there exists the problem identified by the first set of diagnostic data and wherein the type of signal is selected from a set of programmed choices each associated with one of the following macro categories of signal:
voice audio signals;
music audio signals;
noise audio signals.

32. Architecture according to claim 30, wherein the user application acquires a third set (III) of diagnostic data indicating at least one direction of origin of an audio signal affected by the problem.

33. Architecture according to claim 27, wherein the means for processing a new configuration profile of the server (300) process the new configuration data adjusting at least one configuration parameter of the hearing aid by means of an automatic adjustment process programmed on the server (300).

\* \* \* \* \*